United States Patent
Rode et al.

(10) Patent No.: US 6,979,753 B2
(45) Date of Patent: Dec. 27, 2005

(54) PROCESS FOR PREPARATION OF 2-PHENYL ETHANOL

(75) Inventors: Chandrashekhar Vasant Rode, Maharashtra (IN); Vikas Shripat Kshirsagar, Maharashtra (IN); Vilas Hari Rane, Maharashtra (IN); Raghunath Vitthal Chaudhari, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 14 days.

(21) Appl. No.: 10/731,407

(22) Filed: Dec. 10, 2003

(65) Prior Publication Data

US 2005/0131258 A1  Jun. 16, 2005

(51) Int. Cl.[7] ............................................. C07L 27/00
(52) U.S. Cl. ...................................................... 568/814
(58) Field of Search ........................................ 568/814

(56) References Cited

U.S. PATENT DOCUMENTS

| | | | |
|---|---|---|---|
| 3,579,593 A | | 5/1971 | Wood |
| 4,064,186 A | | 12/1977 | Gibson et al. |
| 4,943,667 A | * | 7/1990 | Hoelderich et al. ......... 568/814 |
| 6,166,269 A | | 12/2000 | Chaudhari et al. |

OTHER PUBLICATIONS

Ley, et al., "Recyclable Polyurea-Microencapsulated Pd(0) Nanoparticles: An Efficient Catalyst for Hydrogenolysis of Epoxides", Organic Letters, 5(24), 4665-4668 Coden: Orlef7; ISSN; 1523-7060, 2003, XP002291206.

Verqhese, et al. "Pd-catalyzed Regiospecific Reductive Ring Opening of Epoxides and Glycidic Esters", Synthetic Communications, 25(15), 2267-73, Coden: Syncav; ISSN: 0039-7911, 1995, XP000892321.

Dragovich, et al., "Palladium Catalyzed, Regioselective Reduction of 1,2-Epoxides by Ammonium Formate", J. Org. Chem., vol. 60, 1995, pp. 4922-4924, XP002291208.

Database Beilstein, 'Online! Beilstein Institute for Organic Chemistry, Frankfurt-Main, DE; XP002291209.

Database Beilstein 'Online! Beilstein Institute for Organic Chemistry, Frankfurt-Main, DE; XP002291210.

Database Beilstein 'Online! Beilstein Institute for Organic Chemistry, Frankfurt-Main, DE; XP002291211 & Elsenbaumer et al., J. Org. Chem. vol. 46, No. 20, 1981, pp. 4034-4038.

* cited by examiner

Primary Examiner—Michael L. Shippen
(74) Attorney, Agent, or Firm—Nixon & Vanderhye P.C.

(57) ABSTRACT

The present invention provides an improved process for preparation of 2-phenyl ethanol. More specifically, the present invention relates to a process for preparing 2-phenyl ethanol by catalytic transfer hydrogenation of styrene oxide, in the presence of a supported transition metal catalyst. The catalyst system comprises of a palladium supported on silica, alumina, clay or charcoal.

11 Claims, No Drawings

PROCESS FOR PREPARATION OF 2-PHENYL ETHANOL

FIELD OF INVENTION

The present invention relates to an improved process for preparation of 2-phenyl ethanol. More specifically, the present invention relates to a process for preparing 2-phenyl ethanol by catalytic transfer hydrogenation of styrene oxide, in the presence of a supported transition metal catalyst. The catalyst system comprises of a palladium supported on silica, alumina, clay or charcoal.

BACKGROUND OF THE INVENTION 2-phenyl ethanol (PEA) has a variety of industrial applications. PEA is a colourless liquid possessing a faint but lasting odour of rose petals. Due to this property, 2-phenyl ethanol is important as a fragrance chemical and it is being used in perfumes, deodorants, etc. PEA also has bacteriostatic and antifungicidal properties and is therefore used in the preparation of antiseptic creams and deodorants. PEA is also extensively used in formulation of cosmetics such as hair shampoos and hair dyes to improve texture and quality of hair. 2-phenyl ethanol finds a number of important applications in the manufacture of chemicals such as styrene, phenyl ethyl ester, phenyl acetaldehyde, phenyl acetic acid, benzoic acid, bis-phenyl ether, etc. As it contains an aromatic ring, 2-phenyl ethanol can be nitrated, sulphonated, or chlorinated to give various substituted industrially important compounds.

Several methods for preparing this compound have been described in the literature. The conventional synthetic methods for 2-phenyl ethanol involves Grignard synthesis in which chlorobenzene is converted to phenyl magnesium chloride which reacts with ethylene oxide at 100° C. to give phenyl ethoxy magnesium chloride which is then decomposed with sulphuric acid to give 2-phenyl ethanol. The drawback of this process is the use of hazardous diethyl ether as a solvent. Also, the preparation of phenyl magnesium chloride in situ is very difficult. However, the main problem of this process is the poor quality of the 2-phenyl ethanol, which is not acceptable for perfumery applications. Biphenyl along with rearranged products as the major side products are difficult to separate from 2-phenyl ethanol even by vacuum distillation [Ernet T. Theimer in Fragrance Chemistry, page 271, Academic Press New York (1982)].

Another conventional method for the preparation of 2-phenyl ethanol involves low temperature Friedel Craft alkylation of benzene with ethylene oxide, in the presence of anhydrous $AlCl_3$. This process is operated below 25° C. and thus the molar ratios of the reactants are extremely critical and hence very difficult to maintain these parameters. At a slightly higher temperature, coupling takes place forming a dibenzyl compound. In addition, this process is not an eco-friendly process due to the use of $AlCl_3$ as a reagent [Richard Wilson in Kirk Othmer's Encyclopedia of Chemical Technology Vol. 4, page 116, John Wiley & Sons, New York (1991)], which finally ends up in accumulation of inorganic salts posing environmental problems.

2-phenyl ethanol is also prepared by reduction of styrene oxide using different reducing agents like $LiAlH_4$, $LiAlH_4/AlCl_3$, $B_2H_6$, $LiInH_4$, $NaBH_4$, and $LiBHEt_3$. The use of these reagents leads to the formation of a mixture of primary and secondary alcohols. Reduction of styrene oxide with lithium indium hydride has been reported to give only 33% of 2-phenyl ethanol [Koji Tanaka et al., Tetrahedron letters 36(18), 3169 (1995)].

Catalytic hydrogenation of styrene oxide using both homogeneous and heterogeneous catalysts under hydrogen pressure also has been reported. U.S. Pat. No. 2,822,403 reported catalytic hydrogenation of styrene oxide in the presence of water. Use of emulsifying or dispersing agents was recommended to achieve the required yield. In this process the catalyst used was a combination of Raney nickel and other hydrogenating catalysts like cobalt, platinum and palladium. Similarly, British Patent 760768 and U.S. Pat. No. 3,579,593 describe a process for catalytic hydrogenation of a suspension of styrene oxide in water in presence of combination of Raney nickel and palladium. These processes have several disadvantages like expensive and time consuming distillation, which is required to remove the large amounts of water. Solvent extraction and salting out procedure are rendered difficult due to the presence of emulsifying agents. The greatest disadvantage of the process is the formation of large quantities of ethyl benzene, which destroys the aroma of PEA. In U.S. Pat. No. DE 3,239,611, PEA selectivity was as high as 97% by a two step hydrogenation of styrene oxide and using a combination of acetic acid and triethyl amine as a promoter system.

Catalytic hydrogenation of styrene oxide using hydrogen gas under pressure has been studied previously [U.S. Pat. No. 4,064,186, British Patent 1492257, British Patent 760768]. Recently, almost complete selectivity to PEA has been reported in catalytic hydrogenation of styrene oxide under $H_2$ pressure using palladium supported on carbon in presence of a promoter (NaOH) by Chaudhari et al. [U.S. Pat. No. 6,166,269]. For all these catalytic hydrogenation processes, gaseous hydrogen under pressure is used and an additive is needed to avoid formation of side products. Use of hydrogen under pressure may pose a serious risk of fire or explosion as well as the process is always accompanied with the formation of byproducts. Also, this process requires special high-pressure reactors and is quite uneconomical for laboratory preparations.

The reduction process, in which an organic molecule is used as the hydrogen donor in the presence of a catalyst, is known as catalytic transfer hydrogenation. Compounds like ammonium formate, an aqueous alkaline sodium formate is well known hydrogen donors. Dragovich et al. (J. Org. Chem., 60, 4922, 1995) have reported the use of 10% Pd on activated carbon as a catalyst in the transfer hydrogenation of styrene oxide to 2-phenyl ethanol by ammonium formate and ethanol in which complete reduction of styrene oxide was achieved but with only 58% selectivity to 2-phenyl ethanol. Also, loading of a noble metal (Pd) is.very high, giving TON (turn over number) in the range of 20–80. Iyer et al. (Synth. Comm. 25(15), 2267, 1995) have also studied the transfer hydrogenation of styrene oxide to phenyl ethanol over 5% Pd/C catalyst with methanol and ammonium formate giving TON of 213. Due to the use of methanol as solvent, formation of a by product 1-methoxy ethyl benzene is very likely.

From the above literature, it is clear that there is a scope to have catalytic transfer hydrogenation process for styrene oxide to PEA, to achieve higher selectivity to PEA with higher TON. It is well known that the performance of the heterogeneous catalyst depends on the support used. In all the above-mentioned work on transfer hydrogenation by heterogeneous catalysts, the support used is carbon. In such catalysts, the quality of carbon is very critical in achieving the best activity and selectivity. The properties of carbon depend on the source of carbon and treatment of carbon. Therefore, it is desirable to have a support other than carbon for which the preparation method is standardized leading to higher and consistent activity and selectivity.

The clay support in particular does not need any pretreatment unlike carbon. Also, in the present case, an epoxide is a very reactive species and can undergo various reactions other than hydrogenation to give various side products. Hence, the clay was chosen with certain acidic character in such a way that it would influence the regio selective opening of an epoxide ring to give highest selectivity to 2-phenyl ethanol without using any other additives.

OBJECTS OF THE INVENTION

The main object of the present invention is to provide a process for the selective preparation of 2-phenyl ethanol, which avoids the use of hazardous chemicals like ethylene oxide, aluminium chloride, gaseous hydrogen under pressure etc.

Another object of the present invention is to provide a process using supported catalysts, which could be easily separated from the reaction mixture.

Another object of the present invention is to provide a process with clay as a support for the catalyst which gives almost total selectivity for the desired product, 2-phenyl ethanol.

It is another object of the invention to provide an environmentally friendly process for the preparation of 12-phenyl ethanol.

It is another object of the invention to provide a process for the preparation of PEA which uses a catalyst support with uniform chemical composition prepared by a standard method and then used for the preparation of the hydrogenation catalyst to give high activity and selectivity to the desired product.

SUMMARY OF THE INVENTION

Accordingly, the present invention provides a process for the preparation of 2-phenyl ethanol comprising subjecting a solution of styrene oxide in an organic solvent to catalytic transfer hydrogenation under stirring conditions, over a heterogeneous transition metal catalyst and in the presence of a hydrogen donor, terminating the reaction, separating the catalyst and the 2-phenyl ethanol.

In one embodiment of the invention, the heterogeneous transition metal catalyst contains a metal from platinum group such as platinum, palladium and nickel and a support.

In another embodiment, the concentration of the metal in the catalyst is in the range of 0.02–5.0% (w/w).

In another embodiment catalyst to styrene oxide ratio is in the range of 1:100 to 1:4000.

In another embodiment, support for catalyst is selected from the group consisting of clay, charcoal, silica and alumina.

In yet another embodiments, the support for the catalyst is a saponite clay of the formula $[Na^+_{(x)}\{M^{2+}_{(6)}\}\{Si_{(8-x)}Al_{(x)}\}O_{20}(OH)_4]$ wherein M is magnesium or zinc, x is in the range of 0.2 to 2.0.

In another embodiment, the organic solvent used for preparing the solution of styrene oxide comprises an aliphatic alcohol selected from the group consisting of methanol, ethanol and isopropyl alcohol.

In another embodiment the hydrogen donor compound is selected from the group consisting of aliphatic alcohol, alkali metal and amine esters of fatty acids exemplified by sodium acetate, ammonium formate, sodium formate and potassium formate preferably ammonium formate and sodium formate.

In another embodiment of the invention, the conversion of styrene oxide is complete and the selectivity to 2-phenyl ethanol is $\geqq 99.9\%$ with high TON at milder reaction conditions and also avoiding the use of molecular hydrogen, hazardous material such as diethyl ether, ethylene oxide, and $AlCl_3$ of the conventional process.

In still another embodiment of the invention, the reaction time varies depending on the concentration of the metal in the catalyst and is in the range of 1 to 12 hours.

In another embodiment of the invention, the reaction is carried out at a temperature in the range of 30–80° C. for 1–12 hours.

DETAILED DESCRIPTION OF THE INVENTION

The present invention provides a single step process for preparation of 2-phenyl ethanol [CAS 60-12-8] by catalytic transfer hydrogenation of styrene oxide [CAS 96-09-3] with a transition metal catalyst such as a palladium catalyst supported on clay in presence of a hydrogen donor and a solvent. The reaction is carried out in a temperature range of 30-80° C. under stirring conditions. After completion of the reaction, the reaction mixture is cooled to room temperature, and the catalyst is separated from the product by conventional methods like filtration. Products were analyzed using gas chromatography and also identified by gas chromatograph-mass spectroscopy (GCMS). This method is particularly useful as an alternative to the conventional methods like Grignard synthesis, Friedel-Craft alkylation and also for molecular hydrogen for preparation of 2-phenyl ethanol. This invention eliminates the handling of dangerous hydrogen gas, hazardous diethyl ether solvent, ethylene oxide and the use of $AlCl_3$, which poses serious effluent problems. The invention produces 2-phenyl ethanol selectively via catalytic transfer hydrogenation of styrene oxide using clay supported palladium catalyst.

The present invention provides an improved process for the selective preparation of 2-phenyl ethanol, which avoids the use of hazardous chemicals like ethylene oxide, aluminium chloride, gaseous hydrogen under pressure etc. The catalyst used comprises a supported catalyst which is easily separable from the reaction mixture. The support for the catalyst is preferably clay and the selectivity for the desired product, 2-phenyl ethanol is almost total.

The catalyst used in the invention which comprises palladium supported on clay does not generate any problems relating to the environment, such as heavy metal, when being used to hydrogenate styrene oxide to 2-phenyl ethanol. The catalyst has a uniform chemical composition prepared by a standard method and then used for the preparation of the hydrogenation catalyst to give high activity and selectivity to the desired product.

The process of the present invention also avoids the use of hydrogen under pressure, hazardous material such as diethyl ether, ethylene oxide, and $AlCl_3$, of the conventional process. The present process gives complete conversion of styrene oxide with >99.9% selectivity to 2-phenyl ethanol at milder reaction conditions. The present process achieves a very high selectivity to 2-phenyl ethanol, and it requires merely the filtration of catalyst and distillation of 2-phenyl ethanol of the perfumery grade purity. The conversion and selectivity to PEA was found to be dependent on the supports used for the preparation of the catalysts. PEA selectivity was >99.9% for only clay as a support and for other supports it varied between 40-80% while conversion also varied from 60 to 99.9% depending on support used.

The present invention comprises catalytic transfer hydrogenation of styrene oxide in an organic solvent under stirring conditions, over a supported palladium metal catalyst in presence of a hydrogen donor, preferably at a temperature range of 30–80° C. for 1–12 hours. The catalyst is separated by any conventional method and the product 2-phenyl ethanol separated by distillation.

The heterogeneous catalyst contains a metal from platinum group such as platinum, palladium and nickel and a support. The concentration of the metal in the catalyst is preferably in the range of 0.02–5.0% (w/w) and the catalyst to styrene oxide ratio can be in the range of 1:100 to 1:4000. The support for the catalyst is a saponite clay of the formula, $[Na^+_{(x)}\{M^{2+}_{(6)}\}\{Si_{(8-x)}Al_{(x)}\}O_{20}(OH)_4]$ wherein M can be either magnesium or zinc, x is preferably in the range of 0.2 to 2.0.

The organic solvents used for preparing the solution of styrene oxide are aliphatic alcohols selected from the group containing methanol, isopropyl alcohol or higher alcohols. The hydrogen donor compound are preferably selected from aliphatic alcohols, alkali metal or amine esters of fatty acids exemplified by sodium acetate, ammonium formate, sodium formate and potassium formate preferably ammonium formate and sodium formate.

In a feature of the present process a complete conversion and almost complete selectivity ($\geq 99.9\%$) to 2-phenyl ethanol is obtained with high TON at milder reaction conditions and also avoids the use of molecular hydrogen, hazardous material such as diethyl ether, ethylene oxide, and $AlCl_3$ of the conventional process. In still another feature the reaction time may vary depending on the concentration of the metal in the catalyst and may be in the range of 1 to 12 hours.

The following examples describe specific illustrative embodiments of the present invention, and should not be construed to limit the scope of the invention in any manner.

EXAMPLE 1

This example demonstrates synthesis of saponite type clay support for the metal catalyst. For synthesis of saponite type clay, slurry of sodium silicate (17.962 gm), aluminium nitrate (3.127 gm) and sodium hydroxide (0.391 gm) was made in de-ionized water and stirred for half an hour at 90° C. After being mixed homogeneously, magnesium nitrate (15.827 gm) and urea (15.015 gm) were added. Whole mixture was stirred for 12 hrs. The mixture was cooled, filtered and washed with distilled water and kept over night in aluminium nitrate solution and then again filtered, washed with distilled water and kept for drying for 10 hrs.

EXAMPLE 2

This example demonstrates preparation of catalysts used in transfer hydrogenation of styrene oxide to 2-phenyl ethanol process. For the preparation of 0.5% Pd on clay, a solution of anhydrous palladium chloride (0.04166 gm) in HCl (1N, 10 ml) was obtained by warming for two hrs. This was added drop wise to a stirred hot (80° C.) suspension of clay (4.975 gm) in water (55 ml) and stirred for 5-6 hrs until the supernatant solution becomes colourless. Formaldehyde (4 ml) was added followed by 10% NaOH solution sufficient to make the suspension strongly alkaline and kept under stirring for 2-3 hrs. The catalyst was filtered, washed with distilled water (until the pH became neutral) and dried in an oven at 110° C.

EXAMPLE 3

This example illustrates the effect of concentration of Pd, which is supported on clay for the conversion of styrene oxide to 2-phenyl ethanol. In a typical experiment, styrene oxide 1.2015 gm (10 mmol), isopropyl alcohol 19.771 gm, ammonium formatel 891 gm (30 mmol), Pd on clay 0.200 gm catalyst were charged in a 50 ml two neck round bottom flask. The reaction mixture was stirred at 65° C. After the reaction was complete, the round bottom flak was cooled below ambient temperature and content were discharged. The reaction mixture was filtered and the resulting filtrate was analyzed by gas chromatography and confirmed by GCMS GCIR. The results are given in Table 1.

TABLE 1

| Sr. No. | Pd concn. on support (%) | Reaction time (hrs) | % Conversion | % Selectivity to PEA | TON |
|---|---|---|---|---|---|
| 1 | 0.2 | 8 | 99.7 | >99.9 | 2608.9 |
| 2 | 0.5 | 4.00 | 100 | >99.9 | 1073.3 |
| 3 | 1 | 2.25 | 100 | >99.9 | 485.8 |
| 4 | 2 | 1.50 | 100 | >99.9 | 265.4 |

EXAMPLE 4

This example illustrates the effect of temperature, for the conversion of styrene oxide to 2-phenyl ethanol. In typical experiment, styrene oxide 1.2015 gm (10 mmol), isopropyl alcohol 19.771 gm, ammonium formatel.891 gm (30 mmol), 0.5% Pd on clay catalyst 0.200 gm were charged in a 50 ml two neck round bottom flask. The reaction mixture was stirred at different temperatures. After the reaction was complete, the round bottom flak was cooled below ambient temperature and content were discharged. The reaction mixture was filtered and the resulting filtrate was analyzed by gas chromatography and confirmed by GCMS GCIR. The results are given Table 2.

TABLE 2

| Sr. No. | Reaction temperature (° C.) | Reaction time (hrs) | % Conversion | % Selectivity to PEA |
|---|---|---|---|---|
| 1 | 65 | 4 | 100 | >99.9 |
| 2 | 55 | 8 | 93.75 | >99.9 |
| 3 | 40 | 8 | 61.20 | >99.9 |

EXAMPLE 5

This example illustrates the effect of solvent for the conversion of styrene oxide to 2-phenyl ethanol. In typical experiment, styrene oxide 1.2015 gm (10 mmol), solvent 19.771 gm, ammonium formate 1.891 gm (30 mmol), Pd on clay catalyst 0.200 gm were charged in a 50 ml two neck round bottom flask. The reaction mixture was stirred at 65° C. After the reaction was complete, the round bottom flak was cooled below ambient temperature and content were discharged. The reaction mixture was filtered and the resulting filtrate was analyzed by gas chromatography and confirmed by GCMS GCIR. The results are given in Table 3. The major side product was obtained in case of entry No. 1, 1-hydroxy 2-methoxy and in case of entry No.2, 1-hydroxy 2-ethoxy ethyl benzene.

TABLE 3

| Sr. No. | Solvent | Reaction time (hrs) | % Conversion | % Selectivity to PEA |
|---|---|---|---|---|
| 1 | Methanol | 6 | 100 | 91.8 |
| 2 | Ethanol | 8 | 51.66 | 65.0 |
| 3 | Isopropyl alcohol | 4 | 100 | ≧99.9 |

EXAMPLE 6

This example illustrates the use of Pd/clay and the use of sodium formate, for the conversion of styrene oxide to 2-phenyl ethanol. In typical experiment, styrene oxide 1.201 gm (10 mmol), isopropyl alcohol 19.398 gm, sodium formate 2.040 gm (30 mmol), 0.5% Pd on clay catalyst 0.200 gm were charged in a 50 ml two neck round bottom flask. The reaction mixture was stirred at 65° C. for 8 hrs. After the reaction was complete, the round bottom flak was cooled below ambient temperature and content were discharged. The reaction mixture was filtered and the resulting filtrate was analyzed by gas chromatography and confirmed by GCMS GCIR. The GC analysis of reaction mixture showed 51.7% conversion of styrene oxide while the selectivity of 2-phenyl ethanol obtained was 50.1%. 1-hydroxy 2-isopropoxide ethyl benzene was obtained as a side product.

The Advantages of the Present Invention are
i) This process gives complete selectivity to 2-phenyl ethanol.
ii) Turn over number (TON) for this process is very high (1073).
iii) The process is very convenient to operate since; it does not involve hydrogen gas under pressure.

We claim:

1. A process for the preparation of 2-phenyl ethanol comprising:
    subjecting a solution of styrene oxide in an organic solvent to catalytic transfer hydrogenation under stirring conditions, over a heterogeneous transition metal catalyst and in the presence of a hydrogen donor, wherein the heterogeneous transition metal catalyst contains a metal from the platinum group selected from the group consisting of platinum, palladium, and nickel along with a support,
    wherein the support for the catalyst is a saponite clay of the formula $[Na^+_{(x)}\{M^{2+}_{(6)}\}\{Si_{(8-x)}Al_{(x)}\}O_{20}(OH)_4]$ wherein M is magnesium or zinc, x is in the range of 0.2 to 2.0,
    terminating the reaction, and
    separating catalyst and 2-phenyl ethanol.

2. A process as in claim 1 wherein concentration of metal in catalyst is in the range of 0.02–5.0% (w/w).

3. A process as in claim 1 wherein catalyst to styrene oxide ratio is in the range of 1:100 to 1:4000.

4. A process as in claim 1 wherein the organic solvent used for preparing the solution of styrene oxide comprises an aliphatic alcohol selected from the group consisting of methanol, ethanol and isopropyl alcohol.

5. A process as in claim 1 wherein hydrogen donor compound is selected from the group consisting of aliphatic alcohol alkali metal and amine esters of fatty acids.

6. A process as in claim 5 wherein the hydrogen donor compound is selected from sodium acetate, ammonium formate, sodium formate and potassium formate.

7. A process as in claim 6 wherein the hydrogen donor compound is selected from ammonium formate and sodium formate.

8. A process as in claim 1 wherein the conversion of styrene oxide is complete and the selectivity to 2-phenyl ethanol is ≧99.9% with high TON.

9. A process as in claim 1 wherein use of molecular hydrogen, diethyl ether, ethylene oxide and $AlCl_3$ is avoided.

10. A process as in claim 1 wherein the reaction time is in the range of 1 to 12 hours dependent on the concentration of the metal in the catalyst.

11. A process as in claim 1 wherein the reaction is carried out at a temperature in the range of 30–80° C. for 1–12 hours.

* * * * *